United States Patent [19]
Dunham et al.

[11] Patent Number: 5,762,067
[45] Date of Patent: Jun. 9, 1998

[54] ULTRASONIC ENDOSCOPIC PROBE

[75] Inventors: Paul T. Dunham, Everett, Wash.; Tracy C. Brechbiel, Lake Stevens, Wash.; Calvin R. Zimmerman, Burnham, Pa.; Frank Bentley Oaks, Renton, Wash.

[73] Assignee: Advanced Technology Laboratories, Inc., Bothell, Wash.

[21] Appl. No.: 655,393

[22] Filed: May 30, 1996

[51] Int. Cl.⁶ .................. A61B 8/12; A61B 1/00
[52] U.S. Cl. .................. 128/662.06; 600/148
[58] Field of Search .................. 128/660.1, 662.06; 600/146–152, 141, 142

[56] References Cited

U.S. PATENT DOCUMENTS

| | | | |
|---|---|---|---|
| 3,557,780 | 1/1971 | Sato | 600/148 |
| 3,948,251 | 4/1976 | Hosono | 128/4 |
| 4,078,555 | 3/1978 | Takahashi | 600/148 |
| 4,919,112 | 4/1990 | Siegmund | 128/4 |
| 4,932,394 | 6/1990 | Nanaumi | 600/148 |
| 4,996,975 | 3/1991 | Nakamura | 128/6 |
| 5,014,685 | 5/1991 | Takahashi | 128/4 |
| 5,018,506 | 5/1991 | Danna et al. | 128/4 |
| 5,179,935 | 1/1993 | Miyagi | 128/4 |
| 5,299,559 | 4/1994 | Bruce et al. | 128/4 |
| 5,402,793 | 4/1995 | Gruner et al. | 128/660.1 |
| 5,512,035 | 4/1996 | Konstorum et al. | 600/146 |

*Primary Examiner*—Francis Jaworski
*Attorney, Agent, or Firm*—W. Brinton Yorks, Jr.

[57] ABSTRACT

An ultrasonic endoscopic probe is provided with an articulating distal tip at which and ultrasonic transducer is located. The articulating section of the probe can be locked in an articulated position by a lock control located at a control section of the probe. The locking force is variably selectable by the user, so that the articulating section will be locked in position by a desired force. The articulating section is controlled by cables, which include cable tension adjustments that also serve to delimit the range of articulation. The articulating section is formed of alternating pivot rings with intervening polymeric pivot beads, which provide repetitively smooth articulation. The ultrasonic transducer is rotatable to steer the acoustic scan plane during use, and a sliding membrane between the transducer and its acoustic window allows the transducer to rotate smoothly without sticking.

11 Claims, 9 Drawing Sheets

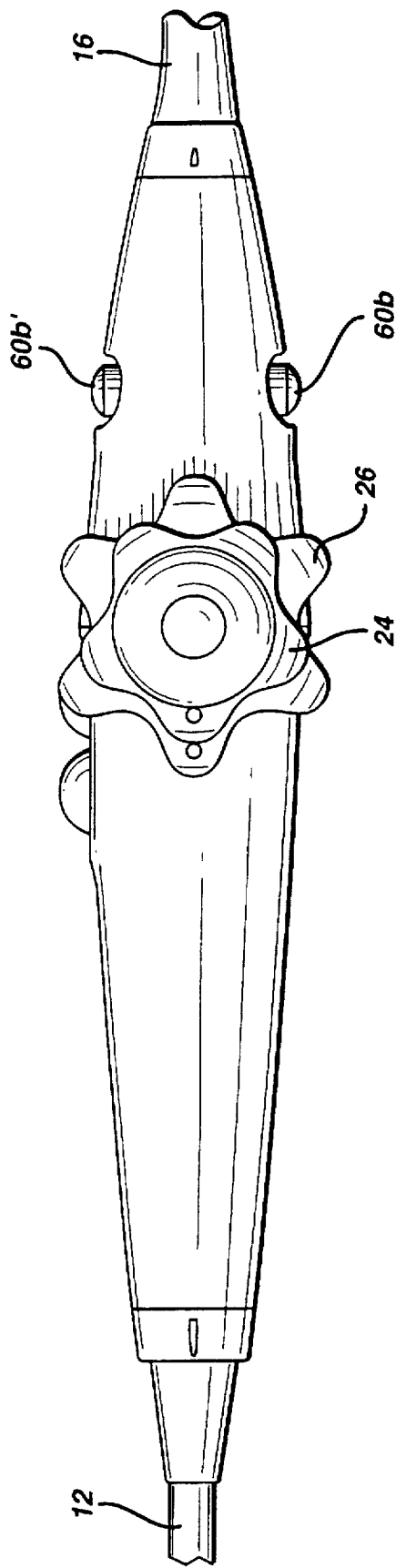
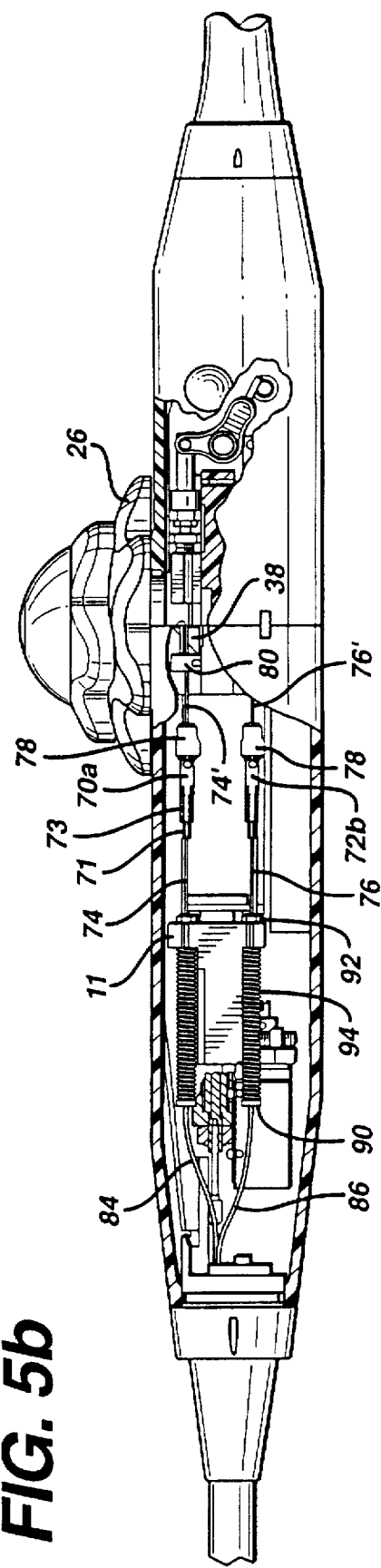
FIG. 5a
FIG. 5b

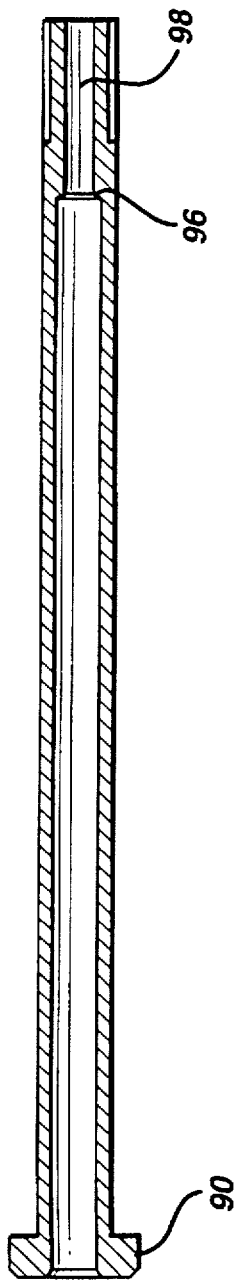
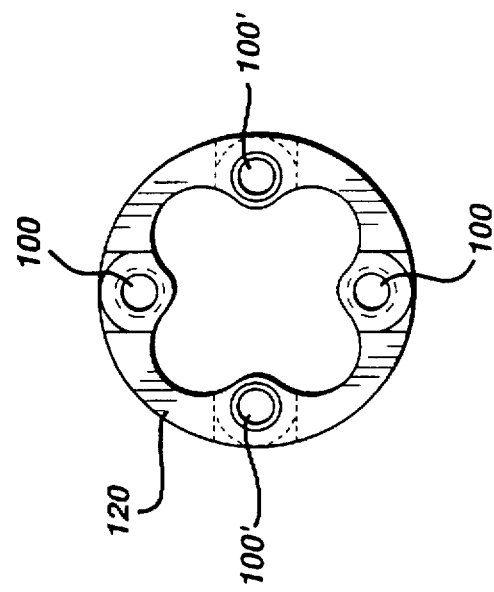
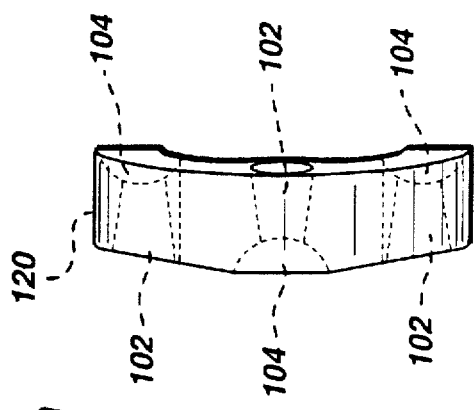

ULTRASONIC ENDOSCOPIC PROBE

This invention relates to ultrasonic endoscopic probes by which an ultrasonic transducer located at the distal tip of an endoscope is manipulated while located within the body from an external control unit.

U.S. Pat. No. 5,479,930 describes an ultrasonic endoscopic probe with an ultrasonic transducer at the distal tip of the probe. The distal tip includes an articulation section which is capable of being articulated in up-down and left-right directions so that the transducer may be remotely moved and aimed at a region of the body which the user desires to image. Once the user has articulated the distal tip with its transducer in the desired manner the articulation section may be locked in its articulated position while the user views ultrasonic images produced from echoes received by the transducer.

In accordance with the principles of the present invention, an improved ultrasonic endoscopic probe is provided which includes a variable force locking mechanism. The articulating section of the distal tip may be locked in a desired position with variable locking forces. The variable locking forces permit the articulating section to yield in response to movement of the body so as to prevent injury when a patient moves, or the probe is accidentally withdrawn from a body cavity of a patient when locked in an articulated position. The locking force is applied by means of a braking surface of one material which engages a different material of an articulation mechanism to prevent binding or seizing of the articulation mechanism. The articulating section is articulated by a control cable which includes a tension adjustment device. The tension adjustment device also serves as a range limiter to limit the range of articulation of the articulating section. The control cable passes through a cable conduit, which is seated in a spring loaded mechanism which absorbs forces which are suddenly applied to the articulating section. The articulating section is formed of a plurality of pivot rings and pivot beads. The rings and beads are made of metallic and polymeric material, respectively, and include apertures which seat the beads in the rings, and through which the control cable passes. The ultrasonic transducer at the distal tip of the probe is rotatable and includes a sliding membrane between the transducer and acoustic window to allow the transducer to rotate smoothly without sticking or binding.

In the drawings:

FIG. 5a is a plan view of the handle of an endoscopic probe of the present invention;

FIG. 5b is partial cutaway side view of the handle of FIG. 5a, showing the cable guide strain relief and cable limit stop arrangements;

FIG. 6 is a cross sectional view of the sleeve for the cable guide strain relief arrangement of FIG. 5;

FIGS. 7a and 7b are side and front views of one of the pivot rings of the articulating section of the probe of FIG. 1;

Figure 1:
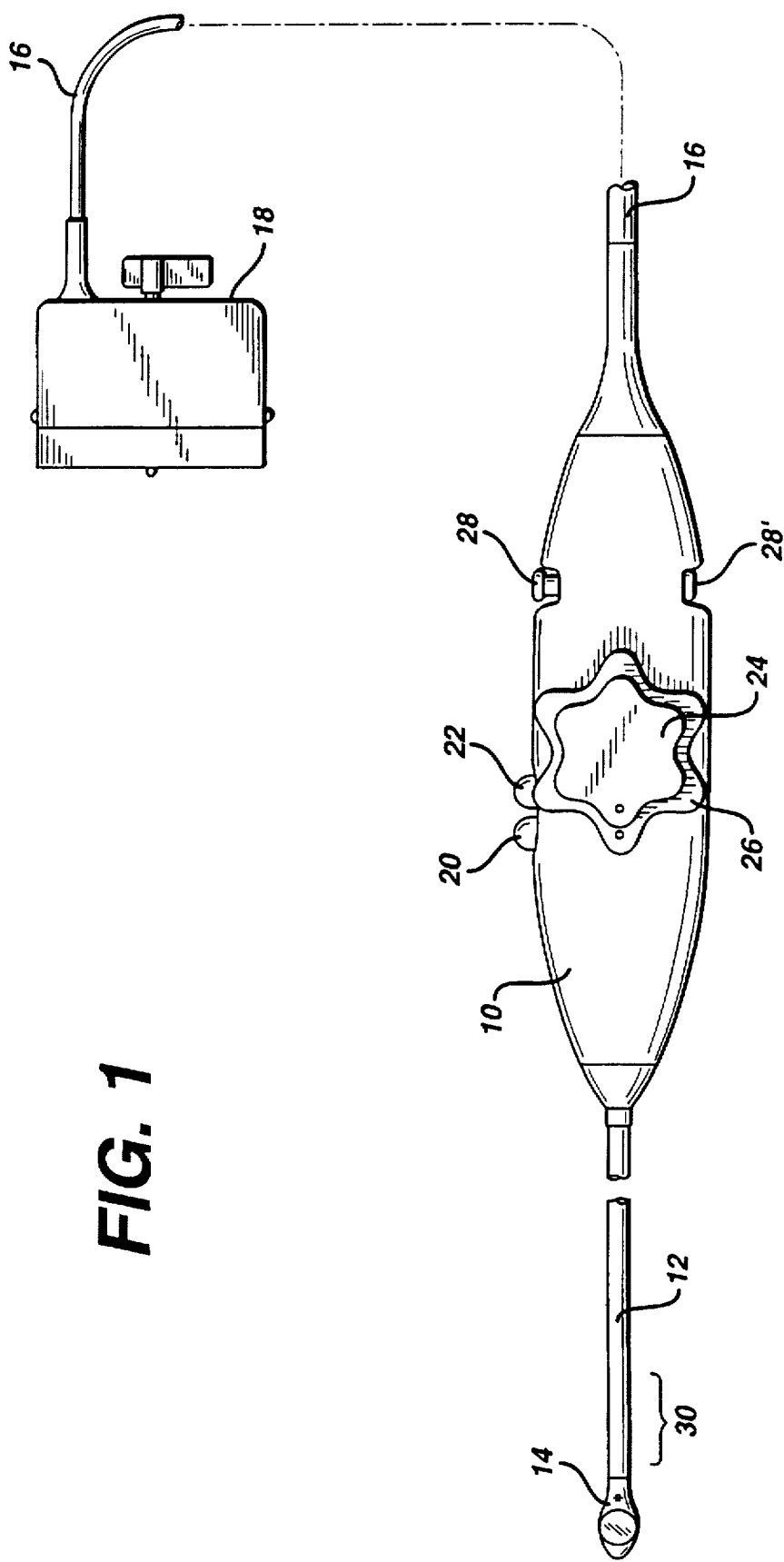
FIG. 1 is a plan view of an endoscopic probe of the present invention.

Referring first to FIG. 1, a plan view of an ultrasonic endoscopic probe is shown. The probe includes a handle 10 where the major controls of the probe are located. Extending from one end of the handle 10 is an endoscope tube 12. The endoscope tube is suitable for insertion into a body cavity such as the esophagus, rectum, or through a surgical incision and can range up to a length of 100 cm. At the end of the endoscope tube 12 is the distal tip 14 of the probe where an ultrasonic transducer is located.

Extending from the other end of the handle 10 is an electrical cable 16 which terminates at a connector 18. The connector 18 is suitable for connecting the probe to an ultrasound system which energizes the probe and displays images formed from the acoustic signals transmitted and received by the transducer at the tip of the probe.

Five of the probe controls are shown in FIG. 1. Two buttons 20 and 22 control selection of the image plane to be scanned by the transducer within the probe tip. The probe tip is connected to the endoscope tube by an articulating section 30 by which the tip can be articulated in any of four directions from the handle by the left-right articulation control knob 24 and the up-down articulation control knob 26. Reciprocating brake buttons 28, 28' are used to lock and unlock the articulating section in any articulated position.

Figure 2:
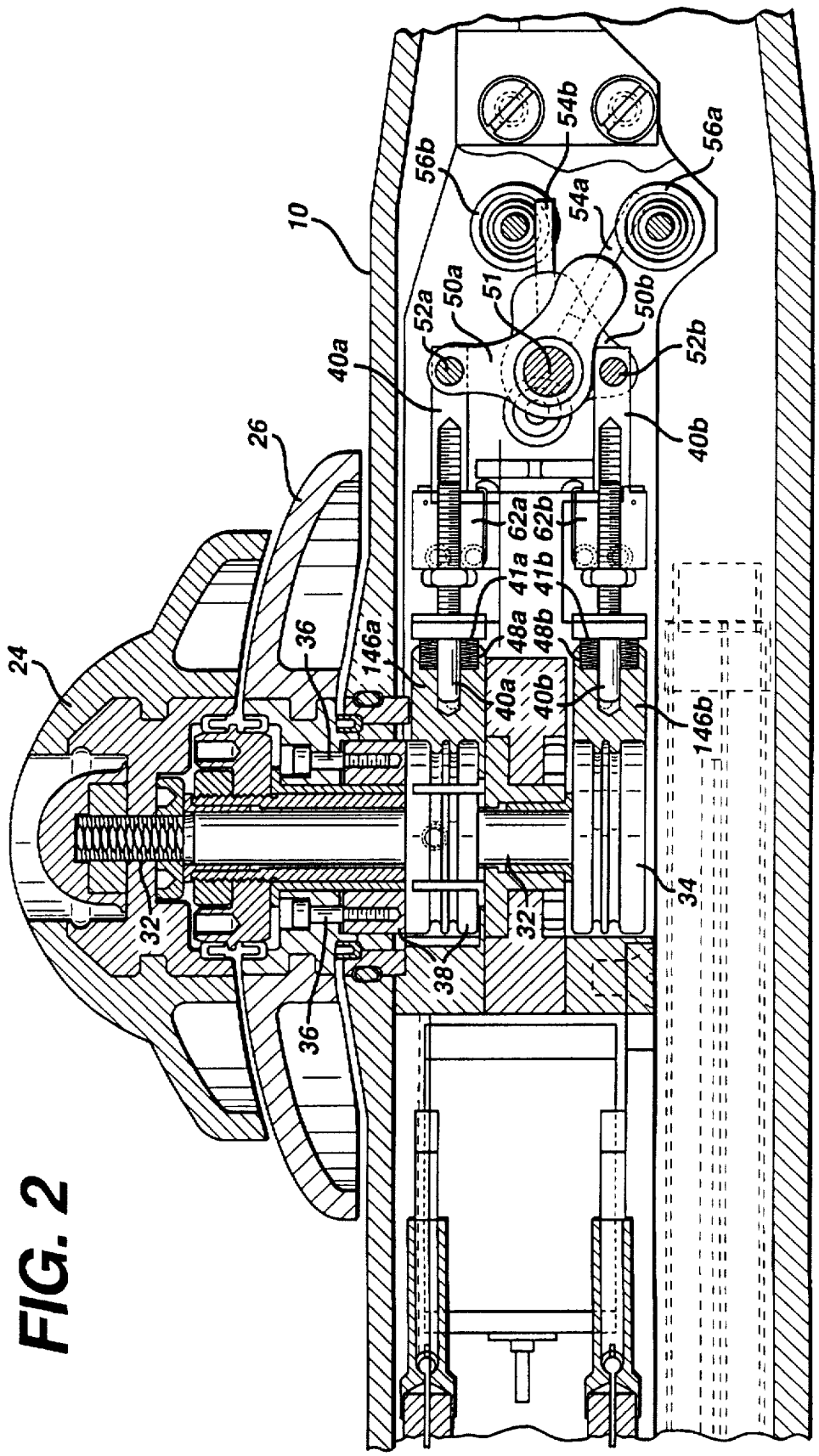
FIG. 2 is a cross-sectional view of the articulation control system of the probe of FIG. 1.

Referring to FIG. 2, a cross-sectional view of the articulation control system of the probe of FIG. 1 is shown. The left-right control knob 24 is attached to one end of a shaft 32. A pulley 34 is connected to the other end of the shaft 32 and is rotated by rotation of the control knob 24. As the pulley is rotated, the cables 76,76' (not shown in this drawing) which are wrapped around and attached to the two grooves of the pulley and extend to the articulating section of the probe are reciprocated. The reciprocation of the cable causes the distal tip 14 of the probe to articulate to the left or the right, depending upon the direction in which the knob 24 is turned.

The up-down control knob 26 is connected by screws 36 to an upper pulley 38. Both the knob 26 and the pulley 38 surround the shaft 32 of the control knob 24 and operate independently therefrom. As the pulley 38 is rotated, the cables 74,74' (not shown in this drawing) which are wrapped around and attached to the two grooves of the pulley and extend to the articulating section of the probe are reciprocated. The reciprocation of this cable causes the distal tip 14 of the probe to articulate up or down, depending upon the direction in which the knob 26 is turned.

Figure 3:
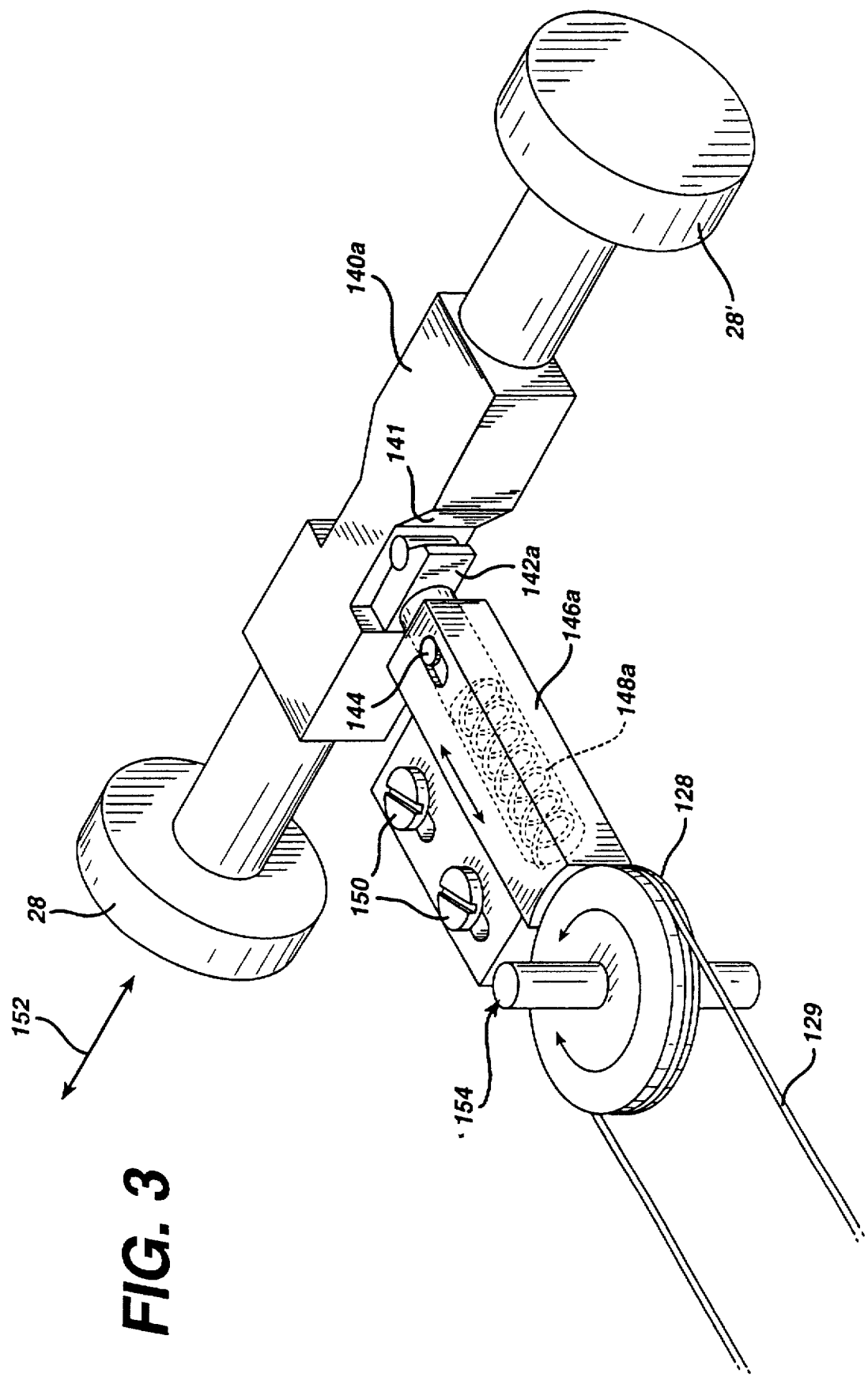
FIG. 3 illustrates the principle of the articulation locking mechanism of an articulating probe.

The handle 10 also contains a locking mechanism by which the articulating section 30 can be locked in a particular articulated or unarticulated position. The principle of the locking mechanism is illustrated in FIG. 3, in which an articulating mechanism pulley 128 and articulation control cable 129 are locked in position by a brake pad 146a. The brake pad 146a is seen to have a concave end surface which engages the circumference of the pulley 128. The brake pad 146a is urged against the pulley 128 by movement of the brake cam 140a, which moves in a reciprocating manner as indicated by arrow 152. As the brake cam is moved to the upper left, a cam follower 142a is depressed by surface 141 of the brake cam 140a. The cam follower in turn compresses a spring 148a inside the body of the brake pad 146a, causing the brake pad to bear more forcefully against the circumference of the pulley 128, thereby impeding its rotation and articulation of the distal end of the probe.

Referring back to FIG. 2, the upper and lower pulleys 38 and 34 are engaged by brake pads 146a and 146b, respectively. To avoid binding or seizing of the lock mechanism due to a metal on metal contact, the concave surfaces of the brake pads are lined with a layer of a polymeric material. This enables the pulleys to be turned smoothly when engaged lightly by the brake pads. Apertures are located in the sides of the brake pads opposite the concave surfaces. Each aperture is engaged by a push rod 40a, 40b. Each push rod has a flange surface 41a, 41b which compresses a spring 48a, 48b against the brake pad.

The push rods are urged against the brake pads and springs by a pair of pivoting rockers. A long rocker 50a is pivotally connected at a pivot point 52a to push rod 40a. A short rocker 50b is pivotally connected at a pivot point 52b to push rod 40b. The long rocker 50a has a rocker arm 54a which rides on the cam surface of a step cam 56a. The short rocker 50b has a rocker arm 54b which rides on the cam surface of a step cam 56b. Both rockers pivot about a common pivot point 51, chosen in accordance with the positions of the push rods, step cams, and the length of the rocker arms of the rockers.

Figure 4:
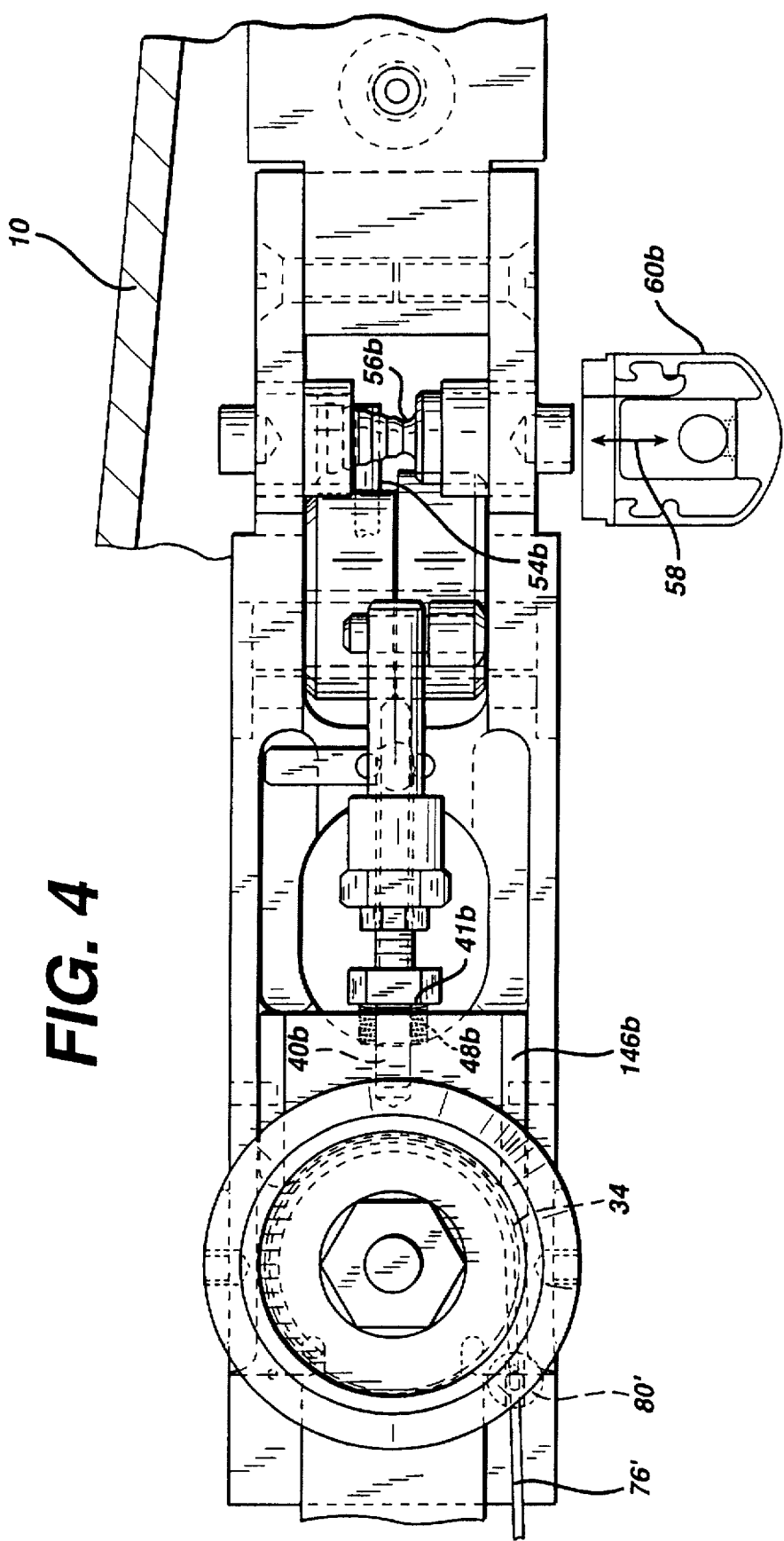
FIG. 4 is a plan view of the variable force articulation locking mechanism of the present invention.

The step cams have a number of discrete steps in diameter along their length, represented by the concentric circles in FIG. 2 and clearly shown in the plan view of FIG. 4 for step cam 56b. The step cams are moved transversely across the body of the handle 10 as indicated by the directional arrow 58. At either end of each step cam is a button, one of which, 60b, is shown in FIG. 4. As the button 60b is depressed and the step cam 56b moves upward in the drawing, the rocker arm 54b clicks smoothly to ride on a decreased diameter of the step cam surface. If discrete detent settings are not desired the step cam surface could be made to smoothly vary without steps using, for instance, a threaded mechanism with a thumbwheel for adjustment. As the rocker arm moves to a smaller diameter cam surface the rocker 50b pivots to pull the push rod 40b away from the brake pad 146b. The force on spring 48b is decreased, decreasing the locking force of the brake pad 146b against the lower pulley 34. As the locking force is decreased the upper knob 24 will turn more easily to articulate the articulating section of the probe in the left-right direction.

As the button on the other end of the step cam 56b (not shown in this drawing) is depressed the braking force against the pulley 34 increases. At the highest cam surface (greatest diameter) the pulley 34 is firmly restrained from moving. As discussed in U.S. Pat. No. 5,402,793, this force can be chosen to firmly retain the articulating section in an articulated position, but also to be of a low enough force to be overcome by a forced straightening of the articulating section without injury if the probe is inadvertently withdrawn from the body in an articulated position.

In a preferred embodiment, the force required by the user to engage the articulation brake increases as each successive step of the step cam is attained. Correspondingly, as the brake is released the rocker arm cascades continuously and easily to the full brake release setting. This affords a quick and easy release of the brake in the event of an emergency.

Each push rod 40a, 40b opposes the arm of a microswitch 62a, 62b. When the rocker arm of a rocker is riding on the smallest diameter of the step cam the microswitch for that brake is not actuated. But when the step cam is moved to begin applying a braking force to a pulley, the arm of the associated microswitch is moved by the push rod sufficient to close the microswitch, thereby sending a signal through the cable 16 to the ultrasound system. A warning is then displayed on the ultrasound system display, alerting the user that the "ARTICULATION LOCK IS ENGAGED" so that the user will not inadvertently withdraw the probe from the body of the patient with the articulating section locked in a curved position. This further aids in avoiding patient discomfort or injury.

It will be appreciated that other sensors may be employed in place of the microswitch, such as optical, pressure, or magnetic sensors which will sense when a braking force is being applied to the articulating mechanism.

It is seen that a sequence of "a" suffix brake elements extend to the right of the upper pulley 38, ending with the lower step cam 56a. Correspondingly, the sequence of "b" suffix brake elements extend from the lower pulley 34 and end at the upper positioned step cam 56b. As a result, the upper and lower step cams lock the upper and lower articulation control knobs, respectively. This positional correspondence of the lock buttons and knobs gives the probe handle an intuitive sense of operation, which is significant because the user is generally focusing his attention on the patient or ultrasonic image display while operating the handle controls by touch.

While the previously described arrangement is seen to be a fully mechanical implementation it will be appreciated that other implementations such as electromechanical arrangements are also possible. In place of the step cams, rockers and push rods one could substitute an electrically controlled solenoid arrangement, for instance. Other variations will also be apparent to those skilled in the art.

As previously mentioned, each pulley has two grooves. The articulation control cable is fastened at one end to ride in one groove. The cable then extends through the endoscope tube 12 to a point where it is affixed to or wrapped around a point in the articulating section 30. The cable continues back through the endoscope tube where it is fastened at the other end to ride in the other groove of the pulley.

In order to facilitate adjustment of the cable tension a cable adjuster is inserted in line with the cable just ahead of the pulley. An adjuster 70 is located in line on each side of the cable. One of the adjusters 70a for the up-down control cable 74 is shown in FIG. 5b, as is one of the adjusters 72b for the lower, left-right control cable 76. The other two adjusters (70a', 72b') are on the other side of the handle and are not visible in this drawing. Each adjuster is comprised of male and female threaded parts 71 and 73, which screw together to increase the cable tension and apart to relax the cable tension. The cable length extending to the articulating section of the probe is connected to the distal threaded part 71, and the short remaining cable length 74' which leads to the pulley is connected to the proximal threaded part 73. Just before engaging the pulley groove the short cable length 74' passes through a cable guide 80, which guides the cable into the pulley groove.

The cable adjusters serve a dual purpose. In addition to cable tension adjustment, the adjusters 70 serve as articulation control end stops. The proximal end of the proximal adjuster part 73 is covered with a polymeric sleeve 78 which serves as a bumper. As control knob 26 is turned to articulate the probe by winding cable section 74' onto the pulley 38, the adjuster 70a and bumper sleeve 78 approach the cable guide 80. The end of this range of adjustment is reached when the bumper sleeve 78 contacts the cable guide 80. Thus, an end stop within the handle 10 prevents the imposition of excessive force on the cable 74 and the articulating section of the probe.

When the control knob is turned in the other direction, the adjuster 70a' on the other side of the handle approaches and contacts a cable guide 80' on the other side of the handle as the short cable section 74' at the opposite end of the cable is wound onto its pulley groove. The range of control permitted by the end stops is fixed by the lengths of the terminating cable sections 74'.

The major lengths 74, 76 of the articulation control cables extend through the endoscope tube in cable conduits 84, 86, which are preferably spiral wound conduits formed of wire which is generally square or rectangular in cross section and may also be squarely wound so that the interior cross sectional area of the conduit is square or rectangular, which minimizes friction between the cable and the inner surface of the conduit. Such conduits are more fully described in U.S. Pat. No. 5,450,851.

In an articulating probe of the present invention it is possible for a sudden excessive force to be placed upon the articulation control cables from a variety of causes. One such cause would be dropping the probe so that it lands on its distal tip, with the force of the fall causing the articulation section to bend. To guard against the shock of such a sudden force it is desirable to provide a means for alleviating this sudden force on the cables. In FIG. 5b the end of each cable conduit is seated in a sleeve 90, with the terminus of the cable conduit seated against a narrowing 96 of the internal diameter of the sleeve. The cable 74, 76 passes through the end of the cable conduit and through the proximal smaller diameter portion 98 of the sleeve. The proximal portion of the sleeve is fitted into an aperture of a handle member 11 and held in place by a nut 92 on the threaded proximal end of the sleeve 90. The body of the sleeve 90 is surrounded by a spring 94 which is retained between the flanged distal end of the sleeve and the handle member 11.

When a sudden excessive force is applied to the articulating section of the probe, the force is transmitted to the control cables and their cable conduits. The force is transmitted through the conduit to the terminus of the cable conduit, where it is applied to the sleeve 90 at the narrowing 96 of the sleeve. The force will cause the sleeve to be urged in the proximal direction. As the sleeve 90 moves in this direction the sudden force is damped by compression of the spring 94, which alleviates the sudden buildup of force on the articulation mechanism of the probe.

A preferred implementation of the articulation section 30 is shown in FIGS. 7-10. The preferred embodiment is constructed of a series of pivot rings 120, one of which is shown in FIGS. 7a and 7b. The rings are hollow to permit passage of cables and other connections to the transducer at the tip of the probe. Around the periphery of each ring are four apertures 100. Each aperture is formed of a conical hole 102 and a semi spherical depression 104 as shown in FIG. 7a. Apertures which oppose each other across the ring are paired so that two have the conical hole facing one direction and the other two are reversed. In FIG. 7b apertures 100 are paired, as are apertures 100'.

Figure 8:
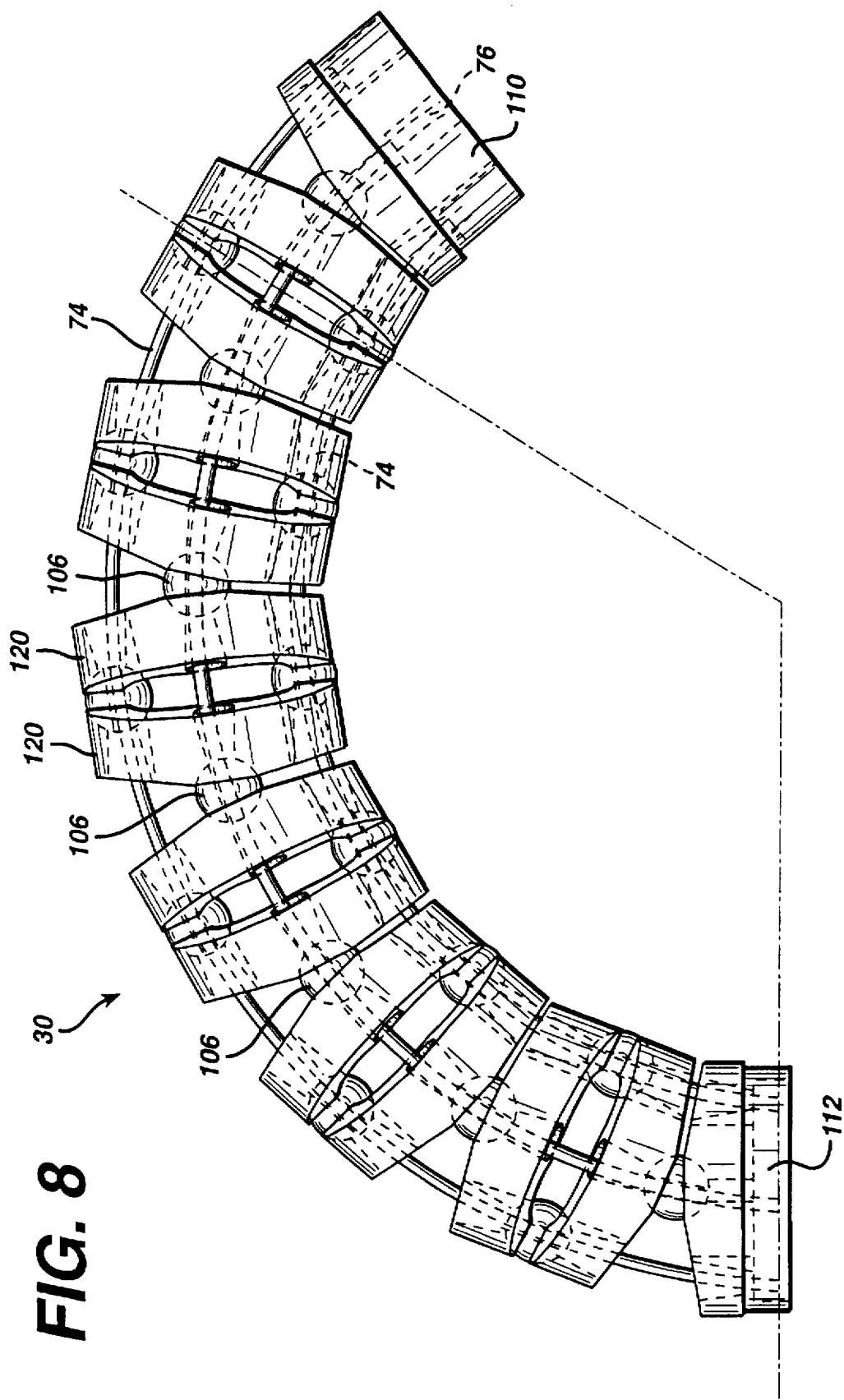
FIG. 8 illustrates the articulating link assembly of the probe of FIG. 1.
Figure 9:
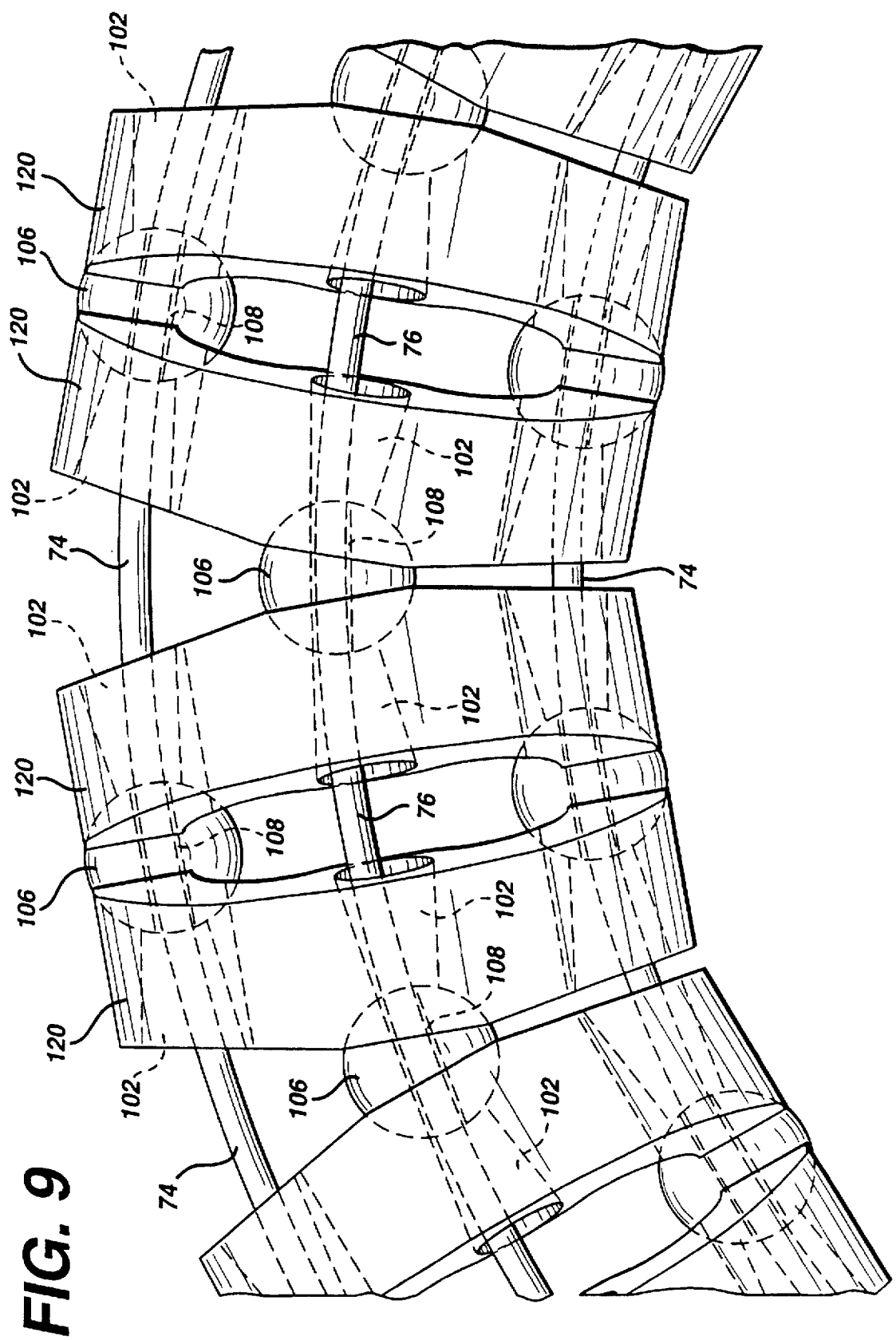
FIG. 9 is an enlarged view of the articulating link assembly of FIG. 8.

The articulating section 30 is constructed by assembling the pivot rings in alternating fashion as shown in FIG. 8. The two semi spherical depressions on one side of a ring oppose two semi spherical depressions on the opposing ring. A polymeric pivot bead 106 formed of a material such as nylon with a diametric hole 108 is seated in each set of opposing semi spherical depressions. The sequence of opposing pivot beads thus alternates 90° in orientation from one side of each ring to the other. The cable conduits of each cable are seated in the proximal end ring 110. The cables exit the conduits and pass through the apertures 100 and pivot bead holes 108 and are terminated at the distal end ring 112.

As the articulating section 30 bends each ring pivots with respect to its neighbor on a pair of pivot beads 106 as shown in FIG. 8. One set of pivot beads accommodates bending in one direction (e.g., up-down) and the next pair of pivot beads accommodates bending in another direction (e.g., left-right.) In FIG. 8 the articulating section is bent down by the tensioning of the lower cable 74.

The conical holes 102 and the pivot beads 106 advantageously accommodate the bending of the articulating section 30 without allowing the cables to rub against the pivot rings. This is more clearly shown in the enlarged view of FIG. 9. There it is seen that the conical shape of the holes 102 provides an expanded opening through which the cables 74 will pass without contacting the pivot rings regardless of the bending of the articulating section. The cables extend from the hole 108 of one pivot bead to the next without any contact with the pivot rings. This permits the articulating section to bend smoothly and wear longer without fraying of the articulation control cables.

Figure 10:
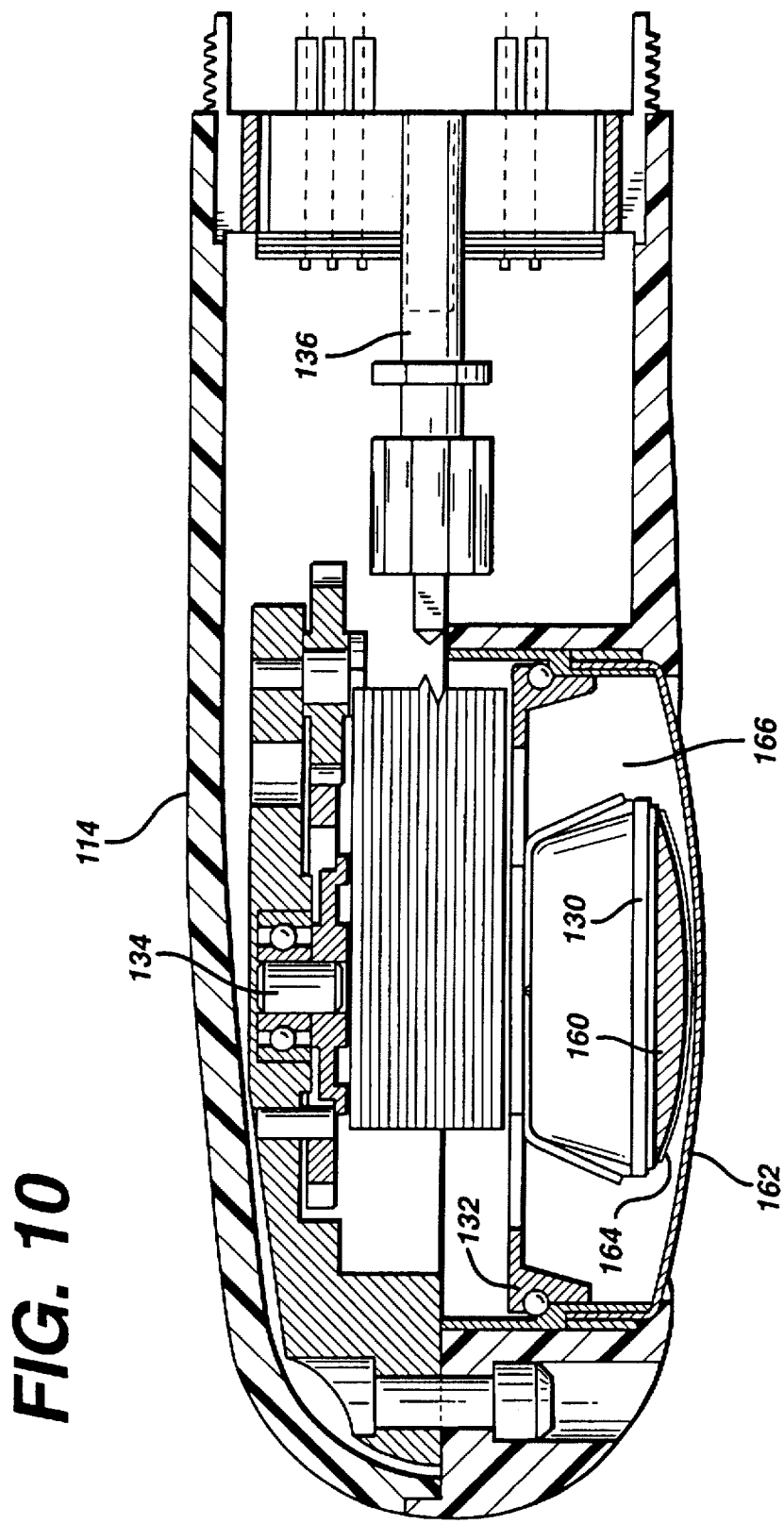
FIG. 10 illustrates the distal tip of the probe in which the ultrasonic transducer is rotatably located.

At the distal end of the articulating section is a housing 114 shown in FIG. 10 which contains the ultrasonic transducer 130. In a preferred embodiment the transducer 130 is an array transducer which is affixed in a rotatable transducer mount 132. The transducer mount rotates on a shaft 134 under control of a drive shaft 136 and gear train. As the user turns the drive shaft 138 from the control section of the probe, preferably through control of a motor which turns the drive shaft, the transducer rotates to change the image plane of the transducer to a new orientation. The transducer 130 is covered with an acoustic matching layer and an acoustic lens 160. The acoustic lens may be made of a material such as a cured RTV compound and provides the transducer with focusing in the elevational direction. The space 166 around the rotating transducer is filled with an acoustic coupling fluid and is sealed with a cover 162 which is durable and exhibits the desired acoustic properties. The cover 162 forms the acoustic window through which ultrasonic energy is transmitted and received by the transducer. Preferably the cover 162 is acoustically transparent and thin so that it will not cause reverberation artifacts from the transmitted ultrasonic waves. A sheet of 1.0 mil Mylar® has been found to possess the desired properties.

As the transducer 130 rotates, it does so in contact with the cover 162. Since the space 166 in which the transducer is located is filed with acoustic fluid, which is often an oil-based compound with lubricating properties, it would be expected that the transducer surface would rotate smoothly against the cover, lubricated as it is by the acoustic fluid. However, the preferred RTV lens material is a non-wetting material, and has been found to adhere to the Mylar cover even in the presence of the acoustic fluid. To overcome this problem the transducer and its acoustic lens are covered with a thin, acoustic membrane 164. A preferred material for the membrane 164 a polymeric material such as 0.1 mil Mylar, shaped to the surface shape of the acoustic lens 160. When the acoustic lens 160 is dome shaped as shown in the drawing, the membrane 164 is also dome shaped and its shape resembles that of a contact lens. When the membrane 164 is made of Mylar and the acoustic lens 160 is made of RTV material, the membrane 164 will stick to the RTV lens and rotate with it. The Mylar lens will not stick to the Mylar cover 162, however, but rotates smoothly against it, aided by an intervening thin layer of the acoustic fluid. Thus, the transducer with its Mylar membrane 164 rotates smoothly against the cover 162 without binding or sticking.

What is claimed is:

1. An ultrasonic endoscopic probe including a control section and an articulating distal end at which an ultrasonic transducer is located, comprising:

a user adjustable control mechanism, located at said control section and coupled to said distal end, for adjusting the articulation of said distal end;

a braking mechanism, located at said control section and coupled to said control mechanism, for applying a braking force to said control mechanism to lock said articulating distal end in an articulating condition; and wherein said braking mechanism further includes means for setting said braking mechanism to apply one of a plurality of different user selectable degrees of braking force to said control mechanism.

2. The ultrasonic endoscopic probe of claim 1, wherein said means for setting said braking mechanism to apply one of a plurality of different user selectable degrees of braking force comprises means for setting a braking force from among a continuously variable range of braking forces.

3. The ultrasonic endoscopic probe of claim 2, wherein said means for setting a braking force from among a continuously variable range of braking forces includes a thumbwheel control.

4. The ultrasonic endoscopic probe of claim 1, wherein said means for setting said braking mechanism to apply one of a plurality of different user selectable degrees of braking force comprises means for setting said braking mechanism to apply one of a finite number of discrete braking forces.

5. The ultrasonic endoscopic probe of claim 4, wherein said means for setting said braking mechanism to apply one of a finite number of discrete braking forces includes a detent mechanism.

6. The ultrasonic endoscopic probe of claim 5, wherein said detent mechanism includes a plurality of cam surfaces.

7. The ultrasonic endoscopic probe of claim 6, wherein said detent mechanism includes a step cam.

8. The ultrasonic endoscopic probe of claim 6, wherein said detent mechanism further includes a cam follower which is adjustable by the user to ride on one of said cam surfaces for setting said braking mechanism to apply one of a finite number of discrete braking forces.

9. The ultrasonic endoscopic probe of claim 8, wherein said cam follower is pivotably mounted to apply different degrees of braking forces to said control mechanism when riding on different ones of said cam surfaces.

10. The ultrasonic endoscopic probe of claim 1, further comprising a warning indicator, coupled to said braking mechanism, for providing an indication when said articulating distal end is locked.

11. An ultrasonic endoscopic probe including a control section and an articulating distal end at which an ultrasonic transducer is located, comprising:

a user adjustable control mechanism, coupled to said distal end, and including a metallic rotating member for adjusting the articulation of said distal end;

a braking mechanism, located at said control section and coupled to said control mechanism, for applying a braking force to said metallic rotating member of said control mechanism to lock said articulating distal end in an articulating condition, wherein said braking mechanism includes a surface contacting said rotating member which is made of a polymeric material to prevent seizing of said rotating member when engaged with a braking force.

* * * * *